United States Patent
Poetter et al.

(10) Patent No.: US 9,354,174 B2
(45) Date of Patent: *May 31, 2016

(54) BIOSENSOR USING WHISPERING GALLERY MODES IN MICROSPHERES

(71) Applicants: GENERA BIOSYSTEMS LIMITED, Scoresby, Victoria (AU); Paul Mulvaney, Parkville, Victoria (AU)

(72) Inventors: Karl Poetter, Northcote (AU); Brendan Toohey, Clifton Hill (AU); Paul Mulvaney, Parkville (AU)

(73) Assignee: GENERA BIOSYSTEMS LIMITED, Scoresby, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/774,298

(22) Filed: Feb. 22, 2013

(65) Prior Publication Data
US 2013/0189706 A1 Jul. 25, 2013

Related U.S. Application Data

(63) Continuation of application No. 11/597,484, filed as application No. PCT/AU2005/000748 on May 26, 2005, now abandoned.

(30) Foreign Application Priority Data

May 26, 2004 (AU) ............................. 2004902818

(51) Int. Cl.
C12Q 1/68 (2006.01)
G01N 21/00 (2006.01)
(Continued)

(52) U.S. Cl.
CPC ............ *G01N 21/6486* (2013.01); *B82Y 10/00* (2013.01); *B82Y 20/00* (2013.01); *G01N 21/7746* (2013.01); *G01N 33/54346* (2013.01)

(58) Field of Classification Search
CPC .................... G01N 21/6486; G01N 33/54366; C12Q 1/6883
USPC ............................... 435/6.1, 287.2; 422/82.07
See application file for complete search history.

(56) References Cited

U.S. PATENT DOCUMENTS 5,117,466 A   5/1992  Buican et al.
5,200,314 A   4/1993  Urdea (Continued)

FOREIGN PATENT DOCUMENTS

WO    WO 01/40757 A2   6/2001
WO    WO 02/13337 A1   2/2002

OTHER PUBLICATIONS

Benner, R.E. et al. 1980 "Observation of structure resonances in the fluorescence spectra from microspheres" *Physical Review Letters* 44:475-478.

(Continued)

*Primary Examiner* — Betty Forman
(74) *Attorney, Agent, or Firm* — Knobbe, Martens, Olson & Bear, LLP

(57) ABSTRACT

A biosensor for detecting the presence of a target analyte is disclosed. The biosensor is formed from microspheroidal particles which have had a binding partner for the target analyte immobilized on their surfaces. The binding partners may be nucleotides; peptides, proteins, enzymes, antibodies and so on. When the analyte binds to its partner, the whispering gallery mode (WGM) profiles of the micro spheroidal particles change such that the profile peaks undergo a red- or blue-shift. The immobilized binding partners may include fluorophores and the like so that they emit fluorescence, phosphorescence, incandescence and the like. These fluorophores may take the form of a nanocrystal or quantum dot.

34 Claims, 5 Drawing Sheets

(51) Int. Cl.
*G01N 21/64* (2006.01)
*B82Y 10/00* (2011.01)
*B82Y 20/00* (2011.01)
*G01N 21/77* (2006.01)
*G01N 33/543* (2006.01)

(56) References Cited

U.S. PATENT DOCUMENTS

| | | | |
|---|---|---|---|
| 5,384,265 | A | 1/1995 | Kidwell et al. |
| 6,544,732 | B1 * | 4/2003 | Chee et al. ............. 435/6.11 |
| 6,551,788 | B1 | 4/2003 | Bell |
| 6,583,399 | B1 | 6/2003 | Hunziker et al. |
| 6,657,731 | B2 | 12/2003 | Tapalian et al. |
| 7,058,103 | B2 | 6/2006 | Ishida et al. |
| 7,901,883 | B2 | 3/2011 | Poetter et al. |
| 8,278,429 | B2 * | 10/2012 | Park et al. ............. 536/23.1 |
| 2001/0026920 | A1 | 10/2001 | Chandler et al. |
| 2002/0068018 | A1 | 6/2002 | Pepper et al. |
| 2002/0172457 | A1 | 11/2002 | Tapalian et al. |
| 2004/0137478 | A1 | 7/2004 | Arnold et al. |
| 2005/0078731 | A1 | 4/2005 | Fan et al. |
| 2005/0191620 | A1 | 9/2005 | McDevitt et al. |
| 2010/0279888 | A1 | 11/2010 | Park et al. |

OTHER PUBLICATIONS

Arnold, S. et al. 2003 "Shift of whispering-gallery modes in microspheres by protein adsorption" *Optics Letters* 28(4):272-274.
Gomez, D.E. et al. 2005 "Tunable Whispering Gallery Mode Emission from Quantum-Dot-Doped Microspheres" *Small* 1(2):238-241.
Hill, S.C. et al. 1984 "Structural resonances observed in the fluorescence emission from small spheres on substrates" *Applied Optics* 23: 1680-1683.
Office Action in corresponding European Application No. 05 742 019.2, dated Oct. 7, 2011.
Vollmer, F. et al. 2003 "Multiplexed DNA quantification by spectroscopic shift of two microsphere cavities" *Biophysical J* 85:1974-1979.

* cited by examiner a.

b.

c.

BIOSENSOR USING WHISPERING GALLERY MODES IN MICROSPHERES

BACKGROUND OF THE INVENTION

1. Field of the Invention

The present invention relates generally to the field of analyte detection. More particularly, the present invention relates to the use of changes in the Whispering Gallery Mode (WGM) profiles of microspheroidal particles induced by the analyte binding to an immobilized binding partner on the particle to thereby detect the presence of the analyte. The present invention further relates to multiplexing protocols and to analytes detected by the WGM profile changes.

2. Description of the Prior Art

Bibliographic details of references provided in the subject specification are listed at the end of the specification.

Reference to any prior art in this specification is not, and should not be taken as, an acknowledgment or any form of suggestion that this prior art forms part of the common general knowledge in any country.

Rapid advances in genomics and proteomics has highlighted the inadequacies of traditional labor intensive methods for examining and detecting the interaction between two molecules. There is a necessity to devise extremely sensitive methods for the analysis of the interaction between different molecules and the detection of analytes in a sample. The development of methods which allow such analysis without the need to label one or other or both analytes and/or binding partners thereof, would be particularly desirable.

At present, gene-chips provide a means for high throughput nucleic acid analysis using oligonucleotide arrays immobilized to slides. However, this technology is dependent on the labeling of at least one of the molecules.

Attempts to develop methods and devices for examining the interaction of molecules which are not dependent on the labeling of one or more of the molecules include biosensors, which are most frequently used for examining DNA and/or proteins based on optical methods. See, for example, Baird and Myszka, *J Mol Recognit* 14:261-268, 2001, Rich and Myszka, *J Mol Recognit* 15:352-376, 2002, Li et al. *Science* 299:840-843, 2003 and Lin et al. *Science* 278:840-843, 1997 which describe optical methods including interferometric devices. Malmqvist, *Nature* 361:186-187, 1993 discloses surface plasmon resonance sensors (SPR). SPR detects a limit of <10 pg·mm$^{-2}$ mass loading (Karlsson and Stahlberg, *Anal Biochem* 228:274-280, 1995) and allows real-time detection of biomolecular interactions. However, SPR requires specific and expensive instrumentation and the ability for multiplexed measurements is limited.

The present invention provides reagents and methods for, inter alia, the detection of interactions between analytes and their binding partners without need for labeling of either molecule.

SUMMARY OF THE INVENTION

The present invention provides methods and reagents for, inter alia, detecting molecules in a sample. These molecules are referred to herein as analytes. The presence or structure of the analytes need not be known and hence the subject method is ideal for detecting hitherto unknown binding partners of orphan receptors and potential modulators of nucleic acid expression or protein including enzyme activity, folding, antigenicity or function. The methods of the present invention are predicated, in part, on the phenomenon that optically detectable labels embedded within or onto a microspheroidal particle will display a distinctive Whispering Gallery Mode (WGM) profile. Reference to "optically detectable" includes reference to detection by spectrometric means. When a target analyte interacts with a binding partner immobilized to the microspheroidal particle, the WGM profile changes enabling very sensitive detection of even rare binding events.

WGMs allow only certain wavelengths of light to be emitted from the particle. The result of this phenomenon is that the usual broad emission (10-100 nm wide) bands from, for example, a fluorophore become constrained and appear as a series of sharp peaks corresponding effectively to standing mode patterns of light within the particle. In accordance with the present invention, it has been determined that the WGM profile is extremely sensitive to changes at the surface of the microspheroidal particle and that the WGM profile changes when the microspheroidal particle interacts with analytes or molecules within its environment.

Accordingly, one aspect of the present invention contemplates a method of detecting an analyte, said method comprising contacting at least one set of microspheroidal particles with a sample putatively comprising said analyte, wherein each particle within a set of microspheroidal particles comprises an optically detectable label and an immobilized putative binding partner of said analyte wherein each particle set has a defined Whispering Gallery Mode (WGM) profile, wherein binding of said analyte to said immobilized binding partner results in a change in said WGM profile of said at least one set of microspheroidal particles which is indicative of the presence of said analyte.

The methods of the present invention may be applied to detect modulation in the WGM profile of a microspheroidal particle wherein said modulation results from detection of binding or other association of molecules in a sample to potential binding particles immobilized to the surface of the microspheroidal particle. Detection of binding reactions between an analyte and its binding partner based on sensitive changes in WGM profiles enables the identification and isolation of the analytes.

A feature of the present invention is that the microspheroidal particles may be excited with a wide range of light sources, facilitating measurement in many different WGM profiles.

An "optically detectable label" may be any molecule, atom or ion which emits fluorescence, phosphorescence and/or incandescence. In one preferred embodiment of the present invention, the optically detectable label is a fluorophore, which may encompass a range of optically detectable labels such as chemical fluorophores and dyes as well as quantum dots.

The present invention also provides a microspheroidal particle as described herein immobilized to a solid support, for example, a solid support may include a microscope slide.

In one specific embodiment, the present invention provides a microspheroidal particle comprising a latex or silica particle which is 1 μm to 100 μm in diameter, labeled with an optically detectable label, such as a fluorophore or quantum dot, the particle further comprising a putative binding partner of an analyte to be detected. The optically detectable label is detectable at visible wavelengths and the microspheroidal particle exhibits one or more WGM profiles. One or more of the WGM profiles of the microspheroidal particle detectably modulates when analytes interacts with the immobilized binding partner on the particle. Any such change in WGM profile is indicative of the presence of an analyte which has bound to its binding partner.

Examples of analytes and binding partners include chemical molecules, nucleic acid molecules, proteins, lipids, fatty acids and carbohydrates.

The subject method of the present invention does not require any knowledge of the existence, presence or structure of the analyte. For example, if it is desired to find a molecule (i.e. an analyte) which interacts with an enzyme or the catalytic site of an enzyme or at or near an antigenic epitope of an enzyme or protein, then the subject method does not require knowledge of whether such an analyte exists. In that case, the microspheroidal particle will carry the target binding partner at or near its surface and changes in WGM profiles used to detect an analyte in a sample such as a combinational library, chemical library or natural product source (e.g. environmental sample, serum, plasma or biological extract) which interacts with the target binding partner.

The present invention enables multiplexing by incorporating multiple sets of microspheroidal particles wherein each set comprises particles of different sizes and/or labeled with different fluorochromes and/or different target binding partners.

The present invention further provides analytes identified by the subject method and kits useful for practicing the subject method.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

A list of abbreviations used herein is provided in Table 1.

TABLE 1

Abbreviations

| Abbreviation | Description |
| --- | --- |
| APS | Aminopropylsilane |
| GAG | Glycosaminoglycan |
| HEX | hexachlorofluorescein |
| HLGAG | Heparin-Like Glycosaminoglycan |
| IR | Infrared |
| JOE | 7'-dimethoxyfluorescein |
| NIR | Near Infrared |
| PEI | Polyethylene imine |
| PSS | Polystyrene sulfonate |
| PVP | Polyvinyl pyrrolidone |
| QD | Quantum Dot |
| SPR | Surface Plasmon Resonance |
| TAMRA | Carboxytetramethylrhodamine |
| TET | Tetrachlorofluorescein |
| TIR | Total Internal Reflection |
| UV | Ultraviolet |
| WGM | Whispering Gallery Mode |

DETAILED DESCRIPTION OF THE PREFERRED EMBODIMENTS

Figure 1:
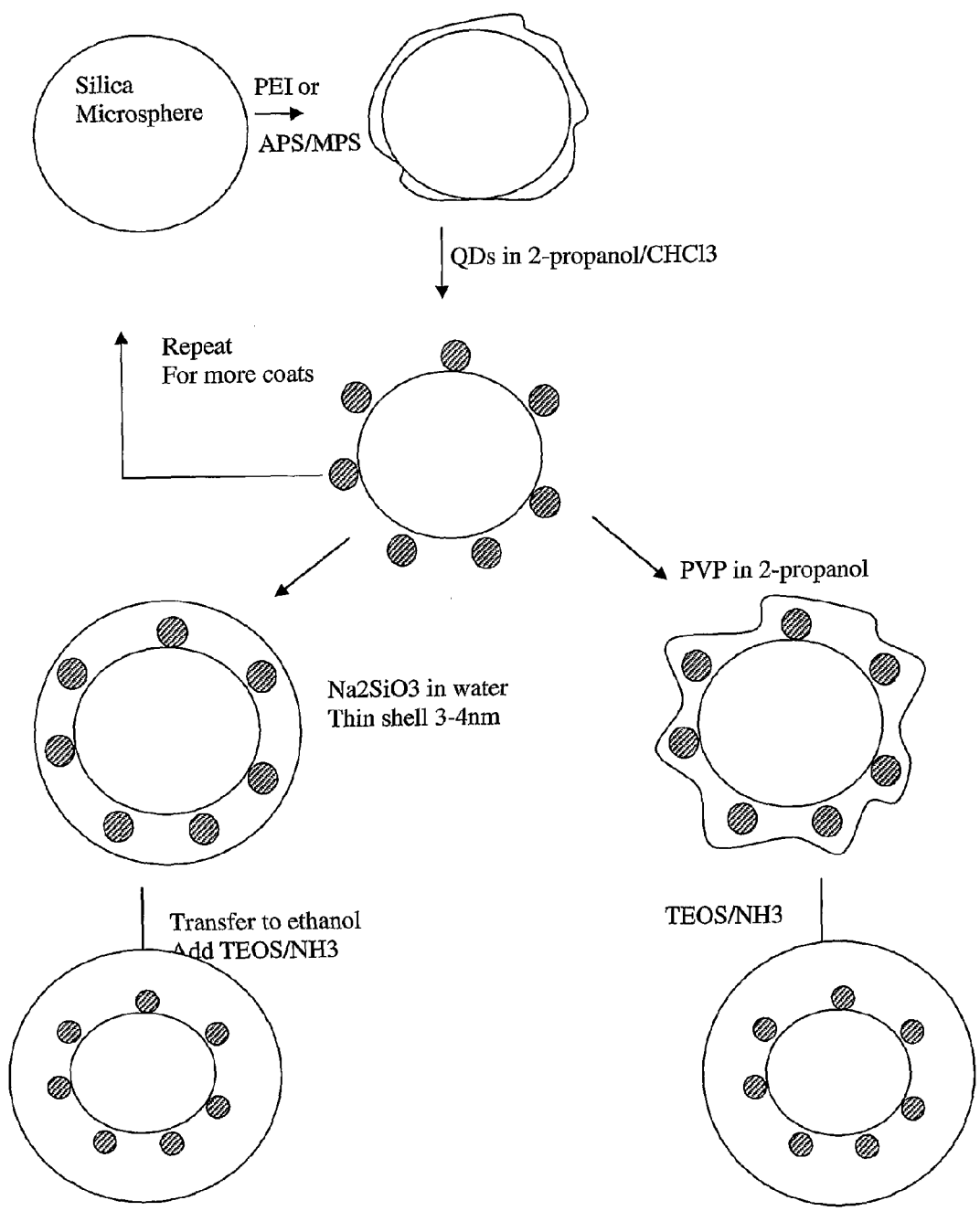
FIG. 1 is a graphical representation showing a schematic of the procedure used to produce Quantum Dot labeled microspheroidal particles.

The present invention provides methods, inter alia, for detecting a molecule referred to herein as an analyte capable of entering into a binding interaction with another molecule referred to as its binding partner immobilized to the surface of a microspheroidal particle labeled with an optically detectable label which confers on the particle a defined WGM profile. Reference to "optically detectable" includes reference to detection by spectrometric means. An interaction between the analyte and the binding partner induces a change by the WGM profile. The methods described herein may be used for detecting analytes in samples and interactions between analytes. Importantly, neither the analyte nor its binding partner require a label. The interaction induces a change in the WGM profile of the microspheroidal particle. The methods of the present invention are predicated, in part, on the phenomenon that fluorescence emitters embedded within or onto a microspheroidal particle establish defined WGM profiles. The microspheroidal particles may be excited by a wide range of light sources. This facilitates measurement in many different configurations and facilitates multiplexing.

WGMs allow only certain wavelengths of light to be emitted from a particle. The result of this phenomenon is that the usual broad emission (10-100 nm wide) bands from a fluorophore becomes constrained and appears as a series of sharp peaks corresponding effectively to standing mode patterns of light within the particle.

The WGM profile is extremely sensitive to interactions or associations with the surface of a the microspheroidal particle. Hence, even rare binding events can be detected due to the change in WGM profile.

It is to be understood that unless otherwise indicated, the subject invention is not limited to specific microspheroidal particle formulations, manufacturing methods, diagnostic or assay protocols, or the like as such may vary. It is also to be understood that the terminology used herein is for the purpose of describing particular embodiments only and is not intended to be limiting. Reference to "an analyte" and a "binding partner" is not to be inferred that any knowledge of the structure of the analyte is known or required to be known.

It must be noted that, as used in the subject specification, the singular forms "a", "an" and "the" include plural aspects unless the context already dictates otherwise. Thus, for example, reference to "a peak" or "a profile" includes a single peak or profile as well as two or more peaks or profile; a "microspheroidal particle" includes a single particle as well as two or more particles; and so forth.

In one aspect, the present invention contemplates a method of detecting an analyte, said method comprising contacting at least one set of microspheroidal particles with a sample putatively comprising said analyte, wherein each particle within a set of microspheroidal particles comprises an optically detectable label and an immobilized putative binding partner of said analyte wherein each particle set has a defined Whispering Gallery Mode (WGM) profile, wherein binding of said analyte to said immobilized binding partner results in a change in said WGM profile of said at least one set of microspheroidal particles which is indicative of the presence of said analyte.

"Microspheroidal particles" contemplated by the present invention include particles comprising any material, homogenous or otherwise which can produce one or more WGM profiles based on its optically detectable label. As will be evident to those of skill in the art, almost any material, homogenous or otherwise may be used for the microspheroidal particle. The microspheroidal particles contemplated herein may also comprise more than one substance, and as such may comprise shells, alloys or mixtures of organic and/or inorganic substances. It is advantageous for quantification of the data generated by the methods of the present invention if the microspheroidal particle comprises a substantially homogenous material with an isotropic refractive index and which is also non-absorbing (other than the optically detectable label, which is further described below).

Particularly useful materials which may be used in accordance with the present invention and which represent specific embodiments of the present invention include materials selected from the list consisting of: silica (for example: quartz or glass), latex, titania, tin dioxide, yttria, alumina, and other binary metal oxides (such as ZnO), perovskites and other piezoelectric metal oxides (such as $BaTiO_3$), ZnS, sucrose, agarose and other polymeric beads. In a particularly preferred embodiment, the "particle" and/or "microspheroidal particle" comprises silica.

In addition, the particles contemplated by the present invention may be produced in any convenient regular or irregular 3-dimensional shape. However, while many shapes of material can sustain WGM profile, it is generally practical to synthesize small spheres or spheroidal particles. Such spheres or spheroidal particles are also referred to herein as "microspheroidal particles" or "microspheres". Accordingly, in preferred embodiments of the present invention, the "particles" and "microspheroidal particles" of the present invention are substantially spherical or spheroidal or comprise a "microsphere".

Although the particles of the present invention may be referred to as "microspheroids" the actual size of the microspheroidal particle depends on a variety of factors and the particles may or may not actually comprise measurements in the micrometer range. In one preferred embodiment the microspheroidal particles of the present invention comprise a diameter (or equivalent measurement in a non-spheroidal particle) of about 1 μm to about 100 μm, including 1 μm, 2 μm, 3 μm, 4 μm, 5 μm, 6 μm, 7 μm, 8 μm, 9 μm, 10 μm, 12 μm, 13 μm, 14 μm, 15 μm, 16 μm, 17 μm, 18 μm, 19 μm, 20 μm, 24 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, 91 μm, 92 μm, 93 μm, 94 μm, 95 μm, 96 μm, 97 μm, 98 μm, 99 μm and 100 μm. Reference to these sizes of microspheres include fractions of the whole numbers. For example, fractions between 1 and 2 μm include 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95 or 2.0.

In a particular embodiment, the microspheroidal particles are microspheres.

A set of microspheroidal particles including a set of microspheres includes a multiplicity (i.e. two or more) particles or microspheres having a common label or size or immobilized binding partner.

As used herein, the term "optically detectable label" refers to any molecule, atom or ion which emits fluorescence, phosphorescence and/or incandescence. The optically detectable label may be chosen to emit at any wavelength at which WGM profile may be easily resolved. This depends on the ratio of the wavelength of the emission to the particle radius. Given that the sphere radius is arbitrary, the emission may be suitably chosen from the ultraviolet (wavelength range of about 350 nm to about 3 nm), visible (wavelength range of about 350 nm to about 800 nm, near infrared (NIR) (wavelength range of about 800 nm to about 1500 nm) and/or infrared (IR) (wavelength range of about 1500 nm to about 10 μm) ranges. However, due to the ease of detection, in one particularly preferred embodiment, the optically detectable label is detectable in the visible wavelength range.

In one particular embodiment, the optically detectable label may be an optically detectable label which emits visible radiation in response to Infrared excitation. Such optically detectable labels are also referred to herein as "upconverters".

Accordingly, another aspect of the present invention provides a method of detecting an analyte, said method comprising contacting at least one set of microspheroidal particles with a sample putatively comprising said analyte, wherein each particle within a set of microspheroidal particles comprises a label with emits visible radiation in response to infrared excitation and an immobilized putative binding partner of said analyte wherein each particle set has a defined Whispering Gallery Mode (WGM) profile, wherein binding of said analyte to said immobilized binding partner results in a change in said WGM profile of said at least one set of microspheroidal particles which is indicative of the presence of said analyte.

The only constraint on the optically detectable label is that the emission in the chosen label should result in cavity mode emission.

In further embodiments of the subject invention, the optically detectable label comprises one or more labels selected from the list consisting of a fluorophore, a semiconductor particle, phosphor particle, a doped particle, or a nanocrystal and a quantum dot. Furthermore, the scattered light from small metal particles (surface plasmon emission) may be used as an optically detectable label.

Accordingly, a further aspect of the present invention is directed to a method of detecting an analyte, said method comprising contacting at least one set of microspheroidal particles with a sample putatively comprising said analyte, wherein each particle within a set of microspheroidal particles comprises an optically detectable label selected from the list consisting of fluorophore, a semiconductor particle, phosphor particle, a doped particle, or a nanocrystal and a quantum dot and an immobilized putative binding partner of said analyte wherein each particle set has a defined Whispering Gallery Mode (WGM) profile, wherein binding of said analyte to said immobilized binding partner results in a change in said WGM profile of said at least one set, of microspheroidal particles which is indicative of the presence of said analyte.

In another embodiment of the present invention, the optically detectable label is a fluorophore. As used herein, the term "fluorophore" refers to any molecule which exhibits the property of fluorescence. For the purposes herein, the term "fluorescence" may be defined as the property of a molecule to absorb light of a particular wavelength and re-emit light of a longer wavelength. The wavelength change relates to an energy loss that takes place in the process. The term "fluorophore" may encompass a range of optically detectable labels such as chemical fluorophores and dyes as well as quantum dots.

In a particular embodiment, the present invention provides a method of detecting an analyte, said method comprising contacting at least one set of microspheroidal particles with a sample putatively comprising said analyte, wherein each particle within a set of microspheroidal particles comprises a fluorophore in the form of a quantum dot and an immobilized putative binding partner of said analyte wherein each particle set has a defined Whispering Gallery Mode (WGM) profile, wherein binding of said analyte to said immobilized binding partner results in a change in said WGM profile of said at least one set of microspheroidal particles which is indicative of the presence of said analyte.

One particularly convenient optically detectable label which may be used in accordance with the present invention is to embed fluorescent particles on or in the microspheroidal particle. These optically detectable label particles may be so small that their properties and emission become size dependent. Such small optically detectable label particles are referred to in the art as semiconductor nanoparticles, quantum dots, quantum wires, quantum rods or nanocrystals or Q-particles. However, as used herein, the term "auantum dot" or "QD" is to be understood to encompass all such particles. Furthermore, optically detectable labels comprising QDs may comprise approximately spherical or spheroidal particles, or coated spherical or spheroidal particles. However, the term QD should not be considered in any way to be limited to a spherical, spheroidal, circular, cylindrical or any other morphology of a "dot". For example, as used herein QDs may also comprise other morphologies including, inter alia, rod-like, ellipsoidal, or coated rod-like or ellipsoidal particles.

QDs consist of a nanometer-scale crystalline core of semiconductor material; biologically active versions are typically surrounded by a protective shell and external coat. For example, QDs may comprise semiconductor crystallites which are about 2 nm to about 30 nm in diameter (e.g. 2, 3, 4, 5, 6, 7, 8, 9, 10, 11, 12, 13, 14, 15, 16, 17, 18, 19, 20, 21, 22, 23, 24, 25, 26, 27, 28, 29 or 30 nm) and may contain approximately 50-500,000 atoms within the crystal, including luminescent crystals comprising materials such as ZnS, ZnSe, ZnTe, CdS, CdSe, CdTe, PbS, PbSe, PbTe, HgS, HgSe, HgTe, Si, ZnO.

QDs fluoresce with a broad absorption spectrum and a narrow emission spectrum. Unlike some other fluorophores, which have distinct absorption spectra, QDs absorb light over a wide spectral range, which allows quantum dots to be excited with a range of light sources, such as lasers, arc lamps, or LEDs. Furthermore, a collection of different QDs can be used in multiplex applications using only a single excitation source. However, the emission spectra for each dot is typically very narrow, in the order of about 30 nm, the exact color depending on the particle's diameter and composition. Furthermore, the narrow emission spectrum of QDs permits spectral resolution of adjacent dots. In addition to the benefits above, QDs are also relatively photostable, even during intense excitation, and are brighter than fluorophores.

In light of the foregoing, it should also be understood that the present invention encompasses the use of different sized QDs in order to optimise the wavelengths at which WGM profiles may be generated in a microspheroidal particle.

Furthermore, the present invention contemplates QDs which are treated with procedures such as thermal treatment, surface modification, alloying, surface passivation or capping with surface coatings to enable the QD to emit with high quantum yield and to improve the photostability for long periods of time.

QDs are also commercially available from companies such as Quantum Dot Corp. (QDC), which produces QDs such as the Qdot [Trade Mark] 605 streptavidin conjugate, containing a cadmium-selenide core that emits at 605 nm. Qdot conjugates that emit at 525, 565, 585, and 655 nm are also available. However, it should be understood that the present invention is not limited in any way by the particular composition of the QD (or any other optically detectable label) and any QD (commercial or otherwise) may be compatible with the present invention.

There are also many fluorescent dyes which are available in the art which may be used as fluorophores in accordance with the present invention. An important property of a fluorescent dye or other fluorophore, which determines it's potential for use is the excitation wavelength of the fluorophore; it must match the available wavelengths of the light source. However, many different fluorescent dyes and other fluorophores will be familiar to those of skill in the art, and the choice of fluorescent marker in no way limits the subject invention.

Convenient "fluorophores" which may be used for the labeling of a microspheroidal particle comprise any fluorescent marker which is excitable using a light source selected from the group below:

(i) Argon ion lasers—comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm amongst others).

(ii) Diode lasers—have an emission wavelength of 635 nm. Other diode lasers which are now available operate at 532 nm. This wavelength excites propidium iodide (PI) optimally. Blue diode lasers emitting light around 476 nm are also available. Such diode lasers may be conveniently employed to excite WGMs within the microspheroidal particles.

(iii) HeNe gas lasers—operate with the red 633 nm line. Such lasers may be conveniently employed to excite WGMs within the microspheroidal particles.

(iv) HeCd lasers—operate at 325 nm. Such lasers may be conveniently employed to excite WGMs within the microspheroidal particles.

(v) 100 W mercury arc lamp—the most efficient light source for excitation of UV dyes like Hoechst and DAPI.

(vi) Xe arc lamps and quartz halogen lamps may likewise be used as a means to excite WGMs and hence utilize the particles as sensors.

In a particular embodiment of the present invention, the fluorescent markers are selected from: Alexa Fluor dyes; BoDipy dyes, including BoDipy 630/650 and BoDipy 650/665; Cy dyes, particularly Cy3, Cy5 and Cy 5.5; 6-FAM (Fluorescein); Fluorescein dT; Hexachlorofluorescein (HEX); 6-carboxy-4',5'-dichloro-2',7'-dimethoxyfluorescein (JOE); Oregon green dyes, including 488-X and 514; Rhodamine dyes, including Rhodamine Green, Rhodamine Red and ROX; Carboxytetramethylrhodamine (TAMRA); Tetrachlorofluorescein (TET); and Texas Red.

Two dyeing techniques are commonly used to fluorescently label microspheroidal particles internal dyeing and external dyeing (surface-labeling). The two techniques produce particles with unique properties, each beneficial for different applications. Internal dyeing produces extremely stable particles with typically narrow fluorescence emissions. These particles often display a greater resistance to photobleaching. As the fluorophore is inside the beads, surface groups are available for use in conjugating ligands (proteins, antibodies, nucleic acids, etc.) to the surface of the bead. For this reason, internally labeled beads are typically used in analyte-detection and immunoassay applications. Surface-labeling involves conjugation of the fluorophore to the microspheroidal particle surface. Because the fluorophores are on the surface of the particle, they are able to interact with their environment just as the fluorophores on a stained cell. The result is a particle standard that exhibits the same excitation and emission properties as stained cell samples, under a variety of different conditions, such as the presence of contaminants or changes in pH. The "environmentally responsive" nature of surface-labeled particles makes them ideally suited for mimicking biological samples. Externally labeled particles are frequently used as controls and standards in a number of applications utilizing fluorescence detection. However, the present invention contemplates the association of a particle with a fluorescent label via any means.

The terms "phosphorescent particles", "phosphor particles" and "phosphors" are used interchangeably herein. What constitutes a phosphorescent optically detectable label would be readily understood by one of skill in the art. However, by way of example, which in no way limits the invention, suitable phosphors include small particles of ZnS, ZnS:Cu, Eu oxide and other phosphors used in display devices.

A optically detectable label comprising a "doped particle" may include a particle which comprises occluded amounts of one or more rare earth ions, such as Eu, Y, Yb, Sm and the like.

As used herein, the term "optically detectable label" should be understood to also encompass multiple optically detectable labels, mixtures of optically detectable labels, coated nanocrystals, alloys and other complex mixtures that would be evident to the skilled artisan. The use of all such optically detectable labels on microspheroidal particles is to be considered as being within the scope of the methods and reagents described herein.

In accordance with the present invention, it has been shown that the emission of any particular label depends on the distribution of the label in the microspheroidal particle, the type of label and the concentration of label. However, the methods of the present invention are still practicable irrespective of whether the optically detectable label is at the surface of the microspheroidal particle, present as a shell within the microspheroidal particle, located at the core of the microspheroidal particle or is present in more than one of the recited locations.

It should be noted that the methods of the present invention are not predicated on quenching of the emission from the optically detectable label. The methods of the present invention, however, are predicated, in part, on a modulation (i.e. a change) in the WGM profile of the optically detectable label as a result of a interaction or association of an analyte with a binding partner immobilized to the surface of a microspheroidal particle.

WGMs, when dealing with electromagnetic radiation, are electromagnetic resonances that can be established when incident light interacts with a particle of higher refractive index than its surrounding medium. WGMs occur at particular resonant wavelengths of light for a given particle size, and the nature of the WGM may change with, inter cilia, the size of the particle containing the WGM and the refractive indices of both the particle and the surrounding medium. Furthermore, the size of the particle can also effect the WGM established therein. WGMs are established when the incident light undergoes total internal reflection at the particle surface.

Total internal reflection (TIR) may occur at the interface between two non-absorbing media. When a beam of light propagating in the medium of higher refractive index meets an interface at a medium of lower refractive index at an angle of incidence above a critical angle, the light is totally reflected at the interface and propagates back into the high refractive index medium. As will be evident to a person skilled in the art, in a 3-dimensional medium the light may be reflected many times within the particle of higher refractive index. In a WGM, the light is concentrated near the circumference of the particle and can be assigned a mode number and a mode order. The mode number, n, provides the number of wavelengths around the circumference of the particle, and the mode order, l, provides the number of maxima in the radial dependence of the electromagnetic field within the particle.

Fluorescence emitters embedded on or within a particle, as defined herein, display defined WGM profiles. These modes allow only certain wavelengths of light to be emitted from the particle. The result of this phenomenon is that the usual relatively broad emission spectrum of an optically detectable label (for example, fluorophores typically emit in a 10-100 nm wide band) becomes constrained and appears as a series of sharp "peaks" corresponding effectively to standing mode patterns of light within the particle. The series of peaks generated as a result of the establishment of a WGM in the microspheroidal particle of the present invention are referred to herein as "Whispering Gallery Mode Profiles" or "WGM Profiles".

The WGM profile is extremely sensitive to both the position of the embedded optically detectable label and their concentration and spatial configuration with respect to each other. Furthermore, particle size and refractive index are also important in determining the emission wavelengths seen in a WGM profile.

It is proposed that the position and amplitude of one or more peaks in a WGM profile may be strongly influenced by interactions or associations of the microspheroidal particle with molecules in a sample or external environment.

In one example, association or binding of a molecule to a microspheroidal particle alters the effective refractive index of the microspheroidal particle altering the WGM profile generated by the microspheroidal particle.

The term "refractive index" would be readily understood by a person of skill in the art. Briefly, the refractive index of a medium is a value calculated from the ratio of the speed of light in a vacuum to that in a second medium of greater density. In the case of a microspheroidal particle, a change in "effective refractive index" may be a change in the refractive index of the complete microspheroidal particle, or a change in effective refractive index may be a change in the refractive index of a region or part of the microspheroidal particle. For example a change in the effective refractive index of a microspheroidal particle may comprise a change in the refractive index of the surface and/or periphery of the microspheroidal particle.

In one particular embodiment, the present invention contemplates a method for detecting the binding or association of a molecule to, or proximal with, the surface or sub-surface of the microspheroidal particle wherein the binding or association of the molecule to an immobilized binding partner of the molecule effects a change in the effective refractive index at the surface of the microspheroidal particle.

A "sub-surface" includes pockets or pores surrounding the particle or which form a co-continuous interface between an internal environment of the particle and an external environment.

In yet another aspect, the present invention relates to the application of the method of the present invention for the detection of changes of the morphology, shape or size of a microspheroidal particle, wherein the microspheroidal particle comprises a particle labeled with an optically detectable label and carries a molecule immobilized to the surface or sub-surface of the particle wherein said microspheroidal particle exhibits one or more WGM profiles and wherein one or more WGM profiles based on the label of said microspheroidal particle detectably alter with a change in the morphology, shape or size of the microspheroidal particle when an analyte interacts with the immobilized molecule; the method comprising:
  (i) determining the initial WGM profile of the microspheroidal particle;
  (ii) subjecting the microspheroidal particle to a putative change in the morphology, shape or size of the microspheroidal particle following a potential interaction between an analyte and the immobilized molecule;
  (iii) determining one or more subsequent WGM profiles of the microspheroidal particle;
wherein modulation in one or more subsequent WGM profile of the microspheroidal particle, relative to the initial WGM profile, is indicative of a change of the morphology, shape or size of the microspheroidal particle and the presence of an analyte associated with the immobilized molecule.

As referred to herein the "morphology, shape or size" of a microspheroidal particle refers to the spatial dimensions of the microspheroidal particle. Accordingly, changes to the morphology, shape or size of a microspheroidal particle include changes in any spatial dimension of the microspheroidal particle including, but not limited to changes in height, width, depth, radius, diameter, circumference and the like.

In yet another aspect, the present invention is directed to a microspheroidal particle comprising a particle labeled with optically detectable label, wherein the microspheroidal particle exhibits a WGM profile and wherein the WGM profile of the microspheroidal particle detectably modulates when an analyte interacts with a molecule immobilized to said microspheroidal particle.

As used herein, the molecule or binding partner immobilized to the microspheroidal particle or the analyte in a sample refers to any chemical entity. Such chemical entities include, but are not limited to small chemical molecule; peptides, polypeptides and proteins or analogs thereof, nucleic acid molecules or analogs thereof, metal atoms or ions or compounds comprising such atoms or ions. Of the nucleic acid molecules, short interfering RNAs (single or double stranded) [siRNAs], interfering RNA complexes (RNAi) and DNA and RNA oligonucleotides are particularly contemplated. Chemical compounds include entities produced in a combinatorial library or in a chemical library. In addition, natural product screening is contemplated from a biological source. Reference to a biological source includes an environmental sample, organism extract, plant or animal extract, serum, urine, exudate, semen, plasma, soil sample, river or sealed sample, extra-terrestrial sample, amongst other sources.

As used herein the phrase "bound to, or otherwise associated with" refers to any process by which a molecule may be associated with a microspheroidal particle. Exemplary modes by which such associations may be mediated include, but are not limited to: covalent binding, hydrogen bonding, van der Waals forces, ionic bonding, metallic bonding, polar bonding and dative (covalent) bonding and the like.

A molecule including a binding partner may also be attached to a microspheroidal particle via an agent that promotes or increases the adsorption or binding of the molecule to the surface of the microspheroidal particle, such an agent is referred to herein as a "linker". For example, polynucleotides may be associated with a microspheroidal particle via a linker which comprises a thiol, amine or carboxyl group. Examples of suitable linkers include amino-terminated silanes such as amino-propyltrimethoxysilane or amino-propyltriethoxysilane. In addition to silanes, compounds such as poly-L-lysine that non-covalently attach to surfaces such as glass and electrostatically adsorb the phosphate groups of a polynucleotide are also within the scope of the present invention. Therefore, other molecules, including other silanes, which are suitable to promote the binding or association of a polynucleotide, polypeptide or other compound to the surface of a microspheroidal particle would be readily identified by the skilled artisan, and the present invention is not limited by the choice of linker.

In one embodiment, the present invention contemplates a microspheroidal particle comprising a particle labeled with an optically detectable label, wherein said microspheroidal particle exhibits a WGM profile and wherein the WGM profile of the microspheroidal particle detectably modulates when a molecule binds or associates with the microspheroidal particle, such as via a molecule comprising a nucleic acid molecule bound to, or otherwise associated with, the surface of the microspheroidal particle.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as a morpholine ring), internucleotide modifications such as uncharged linkages (eg. methyl phosphonates, phosphotriesters, phosphoamidates, carbamates, etc.), charged linkages (eg. phosphorothioates, phosphorodithioates, etc.), pendent moieties (eg. polypeptides), intercalators (eg. acridine, psoralen, etc.), chelators, alkylators and modified linkages (eg. α-anomeric nucleic acids etc.). Also included are synthetic molecules that mimic polynucleotides in their ability to bind a designated sequence via hydrogen bonding and other chemical interactions. Such molecules are known in the art and include, for example, those in which peptide linkages substitute for phosphate linkages in the backbone of the molecule.

Another embodiment of the present invention contemplates a microspheroidal particle as hereinbefore described wherein the microspheroidal particle further comprises DNA bound to, or otherwise associated with, the surface of the microspheroidal particle.

Still a further preferred embodiment of the present invention contemplates a microspheroidal particle as hereinbefore described wherein the microspheroidal particle further comprises RNA or a complex of RNA (e.g. RNA-Rnase complex) bound to, or otherwise associated with, the surface of the microspheroidal particle.

In an alternative embodiment, the present invention contemplates a microspheroidal particle comprising a particle labeled with optically detectable label, wherein the microspheroidal particle exhibits a WGM profile and wherein the WGM profile of the microspheroidal particle detectably modulates when a peptide, polypeptide or protein or analog thereof binds to, or otherwise associated with, the surface of the microspheroidal particle.

In one embodiment, the peptide, polypeptide or protein is an enzyme.

In another embodiment, the peptide, polypeptide or protein is an antibody.

The term "antibody" refers to a protein of the immunoglobulin family that is capable of combining, interacting or otherwise associating with an antigen. An antibody is, therefore, an antigen-binding molecule. The term "antigen" is used herein in its broadest sense to refer to a substance that is capable of reacting with or binding to the antigen-binding site of an antibody. With reference to the present invention, an antigen also includes the idiotype of an antibody.

The term "immunoglobulin" is used herein to refer to a protein consisting of one or more polypeptides substantially encoded by immunoglobulin genes. The recognized immunoglobulin molecules include the κ, λ, α, γ (IgG$_1$, IgG$_2$, IgG$_3$, IgG$_4$), δ, ε and μ constant regions, light chains (κ and l), as well as the myriad immunoglobulin variable regions. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')$_2$ and chimeric antibodies and all of these variants are encompassed by the term "antibody" as used herein. In addition, immunoglobulins from other animals (eg. birds, mammals, fish, amphibians, and reptiles) have similar function, but different nomenclature and these are considered "antibodies" as well.

The present invention also contemplates microspheroidal particles comprising anti-idiotypic antibodies bound to, or otherwise associated therewith. As used herein, the term "anti-idiotypic antibody" refers to an antibody which recognizes and binds to antigenic determinants within the variable region, for example the V$_H$ and/or V$_L$ domains, of a target antibody. These antigenic determinants within the variable region of an antibody are referred to as the "idiotype" of an antibody. Accordingly, an antibody specific for these regions is referred to as an "anti-idiotypic antibody".

"Analogs" of peptides, polypeptides and/or proteins contemplated herein include but are not limited to peptides, polypeptides or proteins comprising modification to side chains, synthetic peptides that incorporate unnatural amino acids and/or their derivatives during synthesis and the use of crosslinkers and other methods which impose conformational constraints on the subject peptide, polypeptide or protein.

Examples of side chain modifications include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphide with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 2.

TABLE 2

Codes for non-conventional amino acids

| Non-Conventional amino acid | Code | Non-Conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |

TABLE 2-continued

Codes for non-conventional amino acids

| Non-Conventional amino acid | Code | Non-Conventional amino acid | Code |
|---|---|---|---|
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenylethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

In yet another alternate preferred embodiment, the present invention contemplates a microspheroidal particle comprising a particle labeled with optically detectable label, wherein the microspheroidal particle exhibits a WGM profile and wherein the WGM profile of the microspheroidal particle detectably modulates when a carbohydrate molecule or analog thereof binds to, or otherwise associates with, the surface of the microspheroidal particle.

In one particularly preferred embodiment, the carbohydrate molecule is a Glycosaminoglycan (GAG) molecule or GAG-like molecule.

GAGs are ubiquitous and play pivotal roles in many of the inflammatory processes within the human body. These large molecular weight polysaccharides contribute to such processes as cancer metastasis, arthritis, transplant rejection and asthma and thus a greater understanding of these processes may lead to improved drugs for the eventual treatment of such conditions. Currently, one of the best known GAGs is the heparin family of sulfated polysaccharides and the anti-coagulant activity of these molecules is well understood.

Heparin-Like GAGs (HLGAGs) are a heterogenous group of molecules (Conrad, Heparin binding proteins. Academic Press, San Diego, 1998; Lander and Selleck, *J Cell Biol* 148(2):227-232, 2000). Heparin and heparan sulfate, like all HLGAGs, are long linear polysaccharides (Sasisekharan and Venkataraman, *Curr Opin Chem Biol* 4(6):626-631, 2000; Casu, *Ann NY Acad Sci* 556:1-17, 1989; Casu, *Adv Carbohydr Chem Biochem* 43:51-134, 1985). They are synthesized as non-sulfated chains of repeating disaccharide units comprising glucuronic acid (GlcA) and glucosamine (GlcN) which, in the golgi, are modified at various sites along their length. Heparin is more extensively modified than heparan sulfate and most of the GlcN units are modified by a sulfate group to become N-sulfated GlcN and most GlcA units are converted to iduronic acid (IdoA) through the action of epimerase. HLGAGs are heterogenous since modifications to the sulfate chains are often incomplete. The result is extensive regions of intermediate modification.

Thus, for example, heparan sulfate chains consist of highly sulfated, structurally flexible domains rich in 2-O-sulfated IdoA alternating with regions of low sulfation consisting predominantly of N-acetyl GlcN and GlcA, which are a rigid structure. The sulfation patterns of HLGAGs are complex especially with respect to the positioning of 6-O-sulfates. Consequently, not all HLGAG molecules are identical. It is the sulfation pattern which largely determines the protein binding characteristics of a particular HLGAG.

Some proteins bind only to particular structural motifs within a HLGAG chain and conversely some GAGs bind only to particular sites or regions on a protein. Anti-thrombin HI, for example, binds to a unique pentasaccharide sequence displaying a particular arrangement of sulfate groups and the heparin pentasaccharide binds to a specific site on the anti-thrombin III protein (Whisstock et al. *J Mol Biol* 301:1287-1305, 2000). Basic fibroblast-derived growth factor (FGF-2) and hepatocyte growth factor (HGF) both bind heparin, but the heparin structures that are essential for binding are quite different for each and are different from that required by anti-thrombin III (Maccarana et al. *J Biol Chem* 268(32): 23898-23905, 1993; Lyon et al. *J Biol Chem* 269:11216-11223, 1994). Moreover, heparin has been shown to bind to a particular region on FGF-2 (Faham et al. *Science* 271:1116-1120, 1996).

FGF-2 recognizes a motif containing a single IdoA 2-O-sulfate in a defined position, whereas for HGF, the positioning of the GlcN 6-O-sulfate groups are critical. Some heparin molecules within a preparation will carry both the anti-thrombin III binding pentasaccharide and the FGF-2 binding motif, whereas others will carry the HGF binding motif and the FGF-2 motif and not the anti-thrombin III binding pentasaccharide. Indeed, on average only one third of the molecules within a preparation of heparin carry the anti-thrombin III binding pentasaccharide (Conrad, 1998, supra).

GAG-like molecules may also be derived from non-mammalian sources. For example, the capsular polysaccharide from *E. coli* K5 is composed of an alternate α-N-acetyl glucosamine (α-GlcNAc) and β-glucuronic acid (β-GlcA) units and contains no sulfate or other charged groups. The heparin backbone consists of the following motif α-GlcNAc, β-GlcA, α-GlcNAc, β-iduronic acid (β-IdoA) with varying degrees of sulfation. The only difference between GlcA and IdoA is the configuration of the carboxylic acid group at C-5, thus the heparin backbone and the *E. coli* K5 backbone are extremely similar in structure.

In yet another aspect, the present invention provides a method of detecting a molecule capable of entering into a binding interaction between a molecule immobilized to, or otherwise associated with, a microspheroidal particle comprising an optically detectable label, as hereinbefore described, and a putative analyte binding partner of said molecule in a sample, said method comprising:

(i) determining a initial WGM profile of the microspheroidal particle comprising the molecule immobilized to, or otherwise associated therewith; and (ii) contacting the microspheroidal particle comprising said immobilized microspheroidal molecule or otherwise associated therewith, with a sample comprising a putative analyte binding partner of said molecule;

wherein a detectable change in the WGM profile of the microspheroidal particle, relative the initial WGM profile, is indicative of binding or interaction between the molecule and the analyte binding partner of the molecule.

As used herein "a detectable change in the WGM profile" may comprise any difference that may be observed between any two WGM profiles.

In one preferred embodiment, the detectable change may comprise a red-shift or blue-shift of one or more peaks in one WGM profile relative to another WGM profile.

As used herein the term "red-shift" refers to the shifting of the point of maximum amplitude of one or more peaks in a WGM profile to a longer wavelength. Despite the name "red", a red-shift may occur in any part of the electromagnetic spectrum and is not limited to visible light. As used herein, the term "red-shift" includes any shifting of a peak to a longer wavelength. Conversely, the term "blue-shift" refers to any movement of a peak to a shorter wavelength.

In a particularly preferred embodiment, the red-shift or blue-shift of a peak in a WGM profile typically comprises a change in the wavelength of the maximum amplitude of the peak of approximately 1 to 100 nm. Reference to 1 to 100 nm includes wavelengths of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 nm. In a particular embodiment, the red-shift or blue-shift of a peak in a WGM profile comprises a change in the wavelength of the maximum amplitude of the peak of approximately 1 to 20 nm, which includes wavelengths of 1, 2, 3, 4, 5, 6, 7, 8, 9, 10, 11, 12, 13, 14, 15, 16, 17, 18, 19 and 20 nm. Although specifically exemplified with respect to wavelength shifts in visible light peaks, the invention also contemplates equivalent and/or proportionate red-shifts and blue-shifts in other regions of the electromagnetic spectrum.

In a further embodiment of the present invention, the change in one or more WGM profiles of a microspheroidal particle, caused by an interaction of an immobilized molecule on the microspheroidal particle with an analyte may comprise the appearance of one or more peaks in one or more of the WGM profiles or the disappearance of one or more peaks in one or more of the WGM profiles.

A WGM profile of a microspheroidal particle as described herein may be ascertained using any convenient method that would be evident to one of skill in the art. Essentially any detection method which can detect one or more wavelengths of electromagnetic radiation may be used to detect a WGM profile. Preferably, the detection means is sufficiently sensitive such that it can differentiate peaks in the WGM profile, more preferably, the detection means can differentiate between two peaks which are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 nm apart. Particularly convenient means which may be used to determine the WGM profile of a microspheroidal particle include a flow-cytometer, array reader and a confocal microscope.

As used herein the term "confocal microscope" includes within its scope, laser scanning confocal microscopes (LSCM) and multiphoton confocal microscopes.

In some embodiments, the WGM profile is determined using a confocal microscope in conjunction with a spectrometer.

In some embodiments, the WGM profile is determined using an array scanner in conjunction with a spectrometer.

The present invention also provides a microspheroidal particle immobilized to a solid support.

Accordingly, in another aspect, the present invention provides a microspheroidal particle comprising a particle labeled with optically detectable label, wherein the microspheroidal particle exhibits a WGM profile and wherein the WGM profile of the microspheroidal particle detectably modulates with said microspheroidal particle is immobilized onto a solid support and/or an analyte interacts with a binding partner captured on the immobilized particle.

As used herein the term "solid support" refers to any solid matrix onto which a microspheroidal particle may be immobilized. In preferred embodiments of the invention, the solid support comprises a solid support which allows the WGM profile of the microspheroidal particle immobilized thereto to be detected. Accordingly, preferable solid supports are those which may be used to immobilize a microspheroidal particle for analysis using a confocal microscope. In a particularly preferred embodiment, the solid support is a microscope slide.

In yet another aspect, the present invention contemplates a microscope slide comprising one or more indentations therein, wherein each indentation is adapted to immobilize a microspheroidal particle as described herein. Preferably, a microspheroidal particle is immobilized onto said slide, by said particle settling into, or embedding into an indentation in said slide.

In yet another aspect, the present invention provides a method of detecting an analyte putatively in a sample, said method comprising:
(i) determining an initial WGM profile of a microspheroidal particle comprising a particle labeled with optically detectable label and a molecule immobilized to or associated therewith, wherein the microspheroidal particle exhibits the WGM profile and wherein the WGM profile of the microspheroidal particle detectably modulates when said microspheroidal binds or otherwise interacts with the analyte putatively in said sample;
(ii) applying said sample to said microspheroidal particle for a time and under conditions to allow interaction of the analyte with the molecule immobilized, or otherwise associated to the microspheroidal particle;
(iii) subsequently determining the WGM profile of the microspheroidal particle;
wherein a detectable change in a the WGM profile relative to an initial WGM profile is indicative of the presence of said analyte in said sample, and an absence of a detectable change in a WGM profile relative to an initial WGM profile is indicative of the absence of said analyte in said sample.

In one embodiment the molecule bound to, or otherwise associated with, the surface of said microspheroidal particle and/or said analyte comprises a nucleic acid molecule. Even more preferably, the nucleic acid molecule is DNA or RNA.

In another preferred embodiment of this aspect of the present invention, the molecules bound to, or otherwise associated with, the surface of the microspheroidal particle and/or said analyte comprises a peptide, polypeptide or protein or analog thereof as defined herein.

In yet another preferred embodiment of this aspect of the present invention, the molecule bound to, or otherwise associated with, the surface of the microspheroidal particle and/or said analyte comprises a carbohydrate molecule. In an even more preferred embodiment, the carbohydrate molecule is a GAG molecule.

In yet another preferred embodiment of this aspect of the subject invention, the molecule bound to, or otherwise associated with, the surface of the microspheroidal particle, and/or said analyte comprises a molecule which binds to, or otherwise interacts with a nucleic acid, peptide, polypeptide, protein and/or carbohydrate molecule.

In yet another aspect of the invention, a method of identifying binding partners of a molecule of interest is provided, said method comprising:
(i) determining a initial WGM profile of a microspheroidal particle comprising a particle labeled with optically detectable label and a molecule immobilized to or associated to therewith;
(ii) applying one or more samples comprising potential binding partners of said molecule of interest to the microspheroidal particle for a time and under conditions to allow interaction of the molecule of interest with the potential binding partner(s);
(iii) subsequently determining the WGM profile of the microspheroidal particle;

wherein modulation of said WGM profile relative to an initial WGM profile indicative of the presence of one or more binding partner(s) in said sample, and an absence of a detectable change in the WGM profile relative to the initial WGM profile is indicative of the absence of one or more binding partner(s) in said sample.

In one preferred embodiment the molecule bound to, or otherwise associated with, the surface of the microspheroidal particle and/or said analyte comprises a nucleic acid molecule. Even more preferably, the nucleic acid molecule is DNA or RNA.

In another preferred embodiment of this aspect of the invention, the molecules bound to, or otherwise associated with, the surface of the microspheroidal particle and/or said analyte comprises a peptide, polypeptide or protein or analog thereof as defined herein.

In yet another preferred embodiment of this aspect of the invention, the molecule bound to, or otherwise associated with, the surface of the microspheroidal particle and/or said analyte comprises a carbohydrate molecule. In an even more preferred embodiment, the carbohydrate molecule is a GAG molecule.

In yet another preferred embodiment of this aspect of the instant invention, the molecule bound to, or otherwise associated with, the surface of the microspheroidal particle, and/or said analyte comprises a molecule which binds to, or otherwise interacts with a nucleic acid, peptide, polypeptide, protein and/or carbohydrate molecule.

The microspheroidal particles of the present invention can be used for the following applications: environmental monitoring, such as water quality (*Legionella, Giardia, Cryptosporidium*, at the source) and point of care diagnostics, airborne pathogens and toxins, protein:protein interaction screening, protein:carbohydrate interaction screening and drug screening, and screening of libraries of small molecules.

The present invention enables multiplexing due to the ability to have two or more sets of microspheroidal particles. The particles in any one set may have a common optically detectable label and/or a common size and/or a common immobilized binding particle. Hence, multiple analytes may be detected using a multiplicity of sets of microspheroidal particles.

The present invention further provides analytes detected by the method of the present invention.

The present invention also further provides kits comprising labeled or pre-labeled microspheroidal particles. The particles may be used in the generation of an assay for detecting changes in an environment surrounding a particle.

The present invention is further described by the following non-limiting examples:

EXAMPLE 1

Production and Labeling of Quantum Dot labeled Microspheroidal Particles

Typically, microspheroidal particles may be prepared by overlaying commercial beads of any desired composition or size with quantum dots. For more robust materials, they should be overcoated with another silica layer to minimize interactions with the medium or adsorbates.

Without limiting the many possibilities, described herein is a typical process used to prepare microspheroidal particles using glass/silica beads.

0.1 g of five micron diameter commercial silica beads were placed in 20 ml 2-propanol and 20 microliters of either mercaptopropylsilane (MPS) or aminopropylsilane (APS) was added. The solution was refluxed at 80° C. to allow chemisorption of the MPS or APS, which led to the creation of mercaptan or amino groups on the bead surface. Excess MPS or APS was removed by centrifugation.

Instead of a silane functionalized bead, the beads can also be activated by adsorbing a cationic polymer. For example without restriction and to illustrate the method, 0.1 g of silica beads were mixed with 20 mL of an aqueous PEI (poly (ethylene imine) solution (1 g/L, 0.5M NaCl). After reacting for one hour, the solution was centrifuged to remove the excess polymer and resuspended in pure water. This procedure was repeated 3 times.

QDs were adsorbed onto the APS or PEI coated beads by adding a suspension of QDs in chloroform to a suspension of the beads in dry 2-propanol. The amount added was such as to coat the beads with about 10 monolayers. The beads and QDs were equilibrated for 10 minutes in a rotation tumbler. Then, the coated beads were separated by centrifugation.

The QD labeled beads can be further stabilized by coating with more silica. This was done in two ways:

First, 5 uL of APS in alkaline water or chloroform (1 mL) was added to the QD coated silica microspheroidal particles and allowed to react for 1 hour with agitation using a rotation tumbler at 0.2 Hz. After removing the excess APS by repeated centrifugation/resuspension cycles in alkaline water or chloroform, 5 mL of "active silica" (5 uL of 2 w/w % sodium silicate in 5 mL of water at pH 8.7) was added to the particles and allowed to react overnight. This resulted in about 3-5 nm of silica being deposited onto the particles. Excess nucleated free silica was separated via centrifugation and the particles redispersed in 2-propanol:water (4:1). Finally the silica layer was increased using TEOS and ammonia as required to obtain the desired thickness.

The second procedure involved direct silica growth in ethanol without a preliminary deposition step in water. This consists of adsorption of PVP and then growth of silica. Enough PVP (MW 30,000) was added to provide 60PVP molecules per $nm^2$ of surface, by dissolving it in chloroform:2-propanol (9:1). This was immediately added to the microspheres, the mixture was sonicated and allowed to react overnight under stirring.

The microspheres were centrifuged (5 sec at 3800 rpm for 5 micron silica) and re-dispersed in 2-propanol (first time). $NH_3$ (4.2%) followed by TEOS (10 vol % in 2-propanol) was added with stirring and left to deposit over 12 hours.

A schematic showing the procedure for producing QD labeled microspheroidal particles is shown in FIG. 1. This generic protocol allows the preparation of photostable, silica microspheres of any practical size from 1 micron up to 100 microns, labeled with one or more different nanoparticles with different emission properties.

Figure 2:
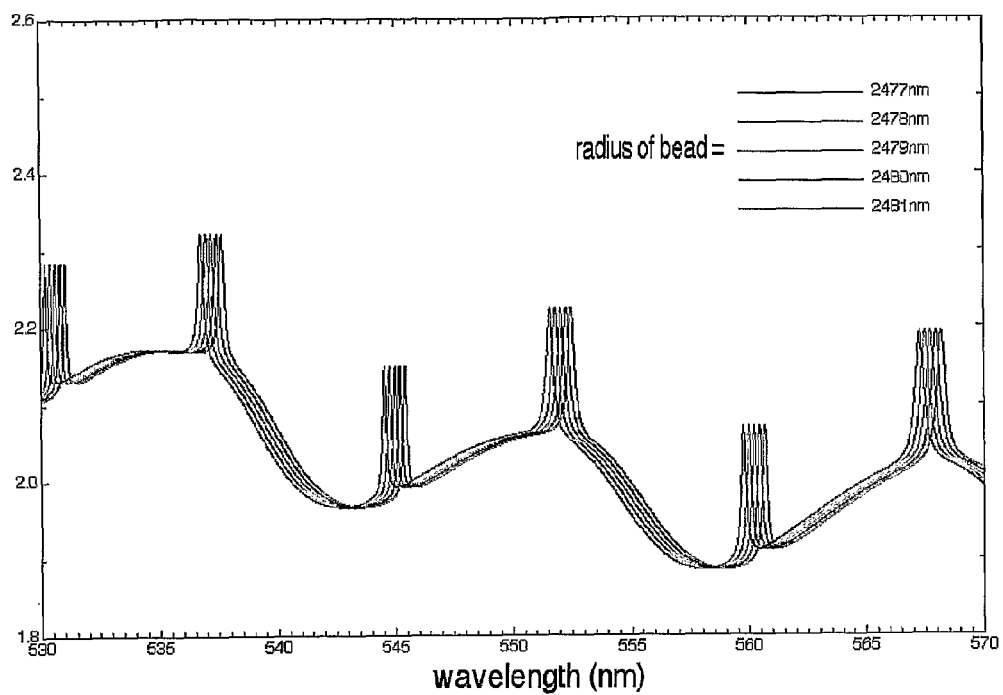
FIG. 2 is a graphical representation showing a calculated curve showing how small changes to the radius of a silica microspheroidal particle lead to clear changes in the calculated WGM profile of the microspheroidal particle.

Examples of QD labeled microspheroidal particles as viewed under a confocal microscope are shown in FIG. 2.

EXAMPLE 2

DNA Detection

Q-Sand beads were conjugated to DNA, forming a complex with a Q-Sand bead and immobilized 48-mer DNA. The fifth base position of the 48-mer was a thymidine base with an incorporated amine. This amine was used to label the DNA with a BODIPY•630/650 NHS ester using a standard condensation reaction. The WGM profile for the Q-Sand bead conjugated to the 48-mer DNA is shown in FIG. 5, panel a.

Figure 5:
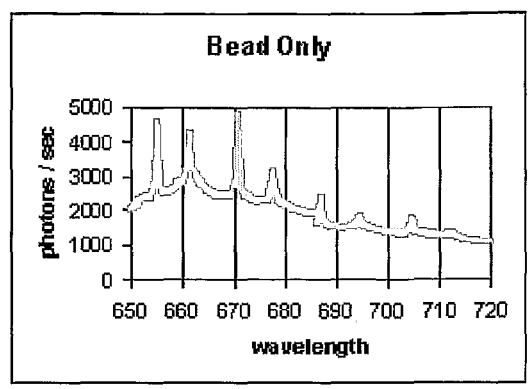
FIG. 5 is a graphical representation of WGM profiles for: (a) DNA was conjugated as 48-mer to Q-Sand particle; (b) Q-Sand beads hybridized to a-Transprobe DNA, the reverse complement of Transprobe; and (c) Q-Sand beads hybridized to a PCR product.
Figure 5:
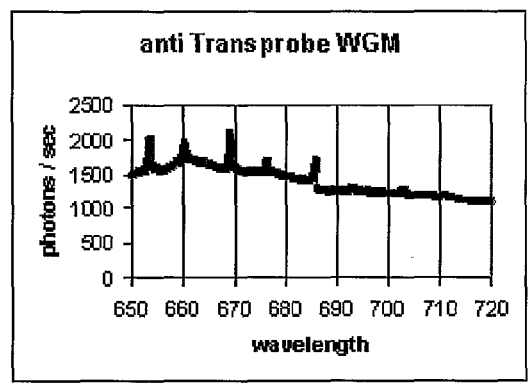
Figure 5:
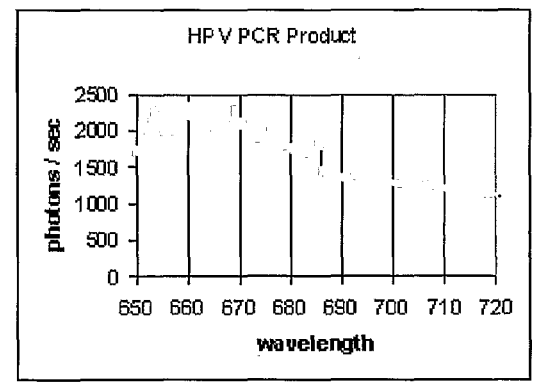

Panel b of FIG. 5 shows the WGM profile of the Q-Sand bead of panel a conjugated to a α-Transprobe DNA which hybridizes to bases 6-24 of the DNA conjugated to the Q-Sand bead. The resulting WGM profile, as seen in panel b of FIG. 5, was a shift of approximately 2.4 nm for all peaks. In addition, the Q-factor (the measure of the quality of the microresonator) reduction was approximately 5×.

Finally, the Q-Sand beads shown in FIG. 5, panel a, were hybridized to a PCR product containing a complementary region to DNA bases 25-48 of the DNA 48-mer. The PCR product was generated from HeLa cell DNA and prepared for hybridization by ExoI and Lambda Exo digestion. The resultant WGM profile was shifted 2.4 nm for all peaks. The Q-factor was approximately 10× drop from Q-Sand only control.

EXAMPLE 3

Surface Functionalization of Silica Microspheroidal Particles

Surface functionalization of silica microspheroidal particles can be done in the same way used for the initial silica microspheroidal particles by refluxing the QD-silica microspheroidal particles in 2-propanol containing MPS or APS or other silane to activate the surface and add functional groups which react with the target bioadsorbate.
Preparation of Conjugates
5 micron microspheroidal particles labeled with orange QDs emitting at 560 nm and overcoated with 10 nm silica were treated with MPS, centrifuged and washed. The microspheres were allowed to react in water with the conjugate, such as a nucleic acid, polypeptide, antibody, carbohydrate or the like for about 1 hour. They were then centrifuged and washed to yield Bioactive QD Microspheres (BQDM).
Binding Assays:
Several BQDM are placed on a microscope slide under a confocal microscope. A drop of reference solution is placed on the microspheres and the spectra collected using 488 nm laser excitation. Then a microliter of a solution containing an agent which putatively interacts with the conjugate on the BQDM is added to the drop and allowed to react over half an hour. The spectrum is collected and any change in the WGM profile, such as a red-shift or blue-shift of one or more peaks, is detected, wherein an observed change is indicative of interaction between the conjugate on the microspheroidal particle and the exogenously added agent.

EXAMPLE 4

Differentiation of Microspheroidal Particles Using WGM Profile

Differentiation by Size
Microspheroidal particles of different sizes were produced using the methods described herein. WGM profiles of each of the different particle sizes were determined using a confocal microscope.

Figure 3:
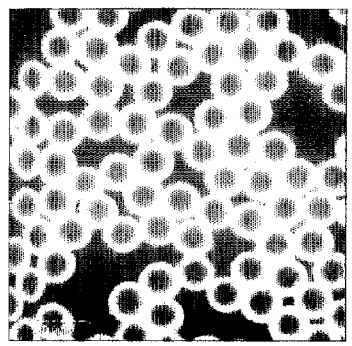
FIG. 3 is a graphical representation showing microspheroidal particles comprising Quantum Dot (QD) optically detectable labels, which exhibit clear distinctive fluorescence and defined WGM profiles.
Figure 3:
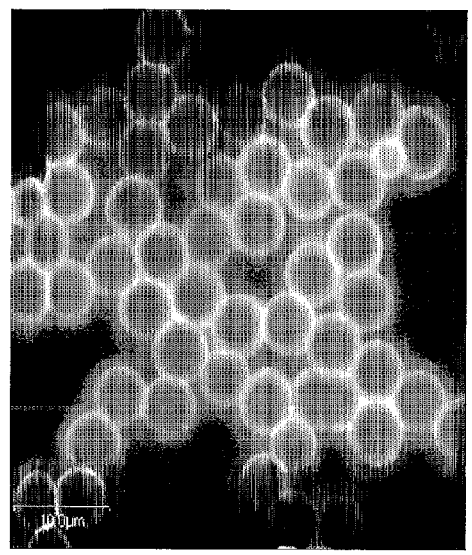

As shown in FIG. 3, the WGM profile exhibited by each of the different sized particles changes with the radius of the microspheroidal particle.
Differentiation by Compound Surface Compound
QD labeled microspheroidal particles comprising different molecules bound to their surface were produced using the methods described herein. WGM profiles of each of the different microspheroidal particles were determined using a confocal microscope.

Figure 4:
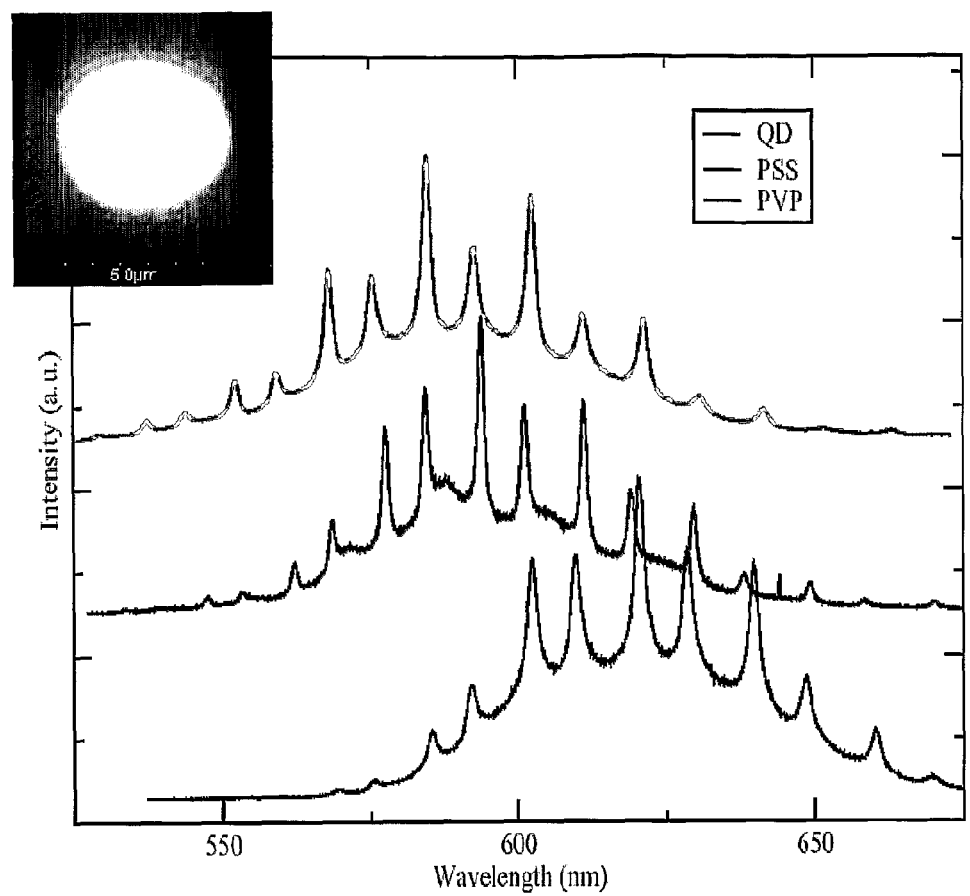
FIG. 4 is a graphical representation showing experimental spectra showing the observed shift in the WGM profile of microspheroidal particle when a monolayer of a biopolymer is adsorbed to the microspheroidal particles. QD=Quantum dot control uncoated microspheroidal particle; PSS=microspheroidal particle with adsorbed monolayer of polystyrene sulfonate (PSS); PVP=microspheroidal particle with adsorbed monolayer of polyvinyl pyrrolidone (PVP).

As shown in FIG. 4, QD refers to a QD labeled microspheroidal particle with no compound bound to the surface, PSS refers to a microspheroidal particle comprising bound polystyrene sulfonate (PSS), while PVP refers to microspheroidal particle with an adsorbed monolayer of polyvinyl pyrrolidone (PVP).

As is evident from the data, the QD labeled microspheroidal particles are sensitive to the binding of a compound to their surface. Furthermore, the WGM profile shift observed also appears sensitive to the nature of the compound binding to the surface.

EXAMPLE 5

The Detection of a Putative Binding Partner in a Sample

Silica microspheres with functional surface sulfhydryl groups are conjugated, via a 5' acrydite molecule, to single stranded oligonucleotides, which have previously been labeled with a fluorescent dye.

The microspheres with attached, labeled oligonucleotide, are then hybridised to complimentary or unrelated oligonucleotides or PCR products.

The hybridised and unhybridised microspheres are extensively washed in Milli Q water and spotted out on a microscope cover slip and allowed to air dry.

The dried microspheres are then examined on a confocal microscope with laser and wavelength filters, appropriate for the fluorescent dyes being used. The whispering gallery modes generated are recorded and compared to determine the wavelength shift in the whispering gallery mode pattern between, microspheres with additional DNA hybridised onto the microsphere surface and microspheres with labeled oligonucleotide attached only.

The resulting shift in the wavelength pattern of the whispering gallery modes can be potentially used to determine the presence or absence of complementary DNA sequences in test samples.

EXAMPLE 6

Screening of Test Compounds

Microspheroidal particles are produced using the protocols described herein. Different beads are identifiable by WGM profile. Even though there is some variability between beads of a particular type, the WGM profile for a given Target with a given fluorescent emitter on a bead of a given size will be almost equivalent. At least 50 different Q-Sand beads can be tested simultaneously.

Microspheroidal particles are arrayed into reaction carriers. These carriers are gridded glass slides with regions for different compounds. The grids are scanned and WGMs are calculated and saved. This reading is the pre-compound control WGM.

Each reaction carrier is tested with one or more of test molecules.

Non-specific binding is alleviated by washing step(s).

After washing the reaction carrier is re-scanned. Positives are identified by WGM shifts compared to pre-test molecule control WGMs.

EXAMPLE 7

Microsphere Synthesis Protocol

Materials:
(3-aminopropyl)trimethoxysilane (APS 99%), (3-mercaptopropyl)trimethoxysilane (MPS, 95%), tetraethyl orthosilicate (TEOS, 98%), polyvinylpyrrolidone (PVP, MW 40,000), Ammonium Hydroxide (29.1% wt % NH3 water) (Sigma-Aldrich). 5 μm silica particles (Bangs Laboratories, Inc.) Chloroform (CH3Cl3) and 2-propanol (AnalaR, Merck, Kilsyth, Victoria).

Instruments:

Olympus Fluorescence Microscope (Olympus, Bonn, Germany), Motorized Rotating Wheel, Shake and Stack (Thermohybaid, Glochester UK), Ultrasonic Cleaner (Cole-Parmer Instrument Company, Illinois, USA).

General Important Notes:

Sterilize all glass-vials and magnetic stirrers with ethanol and allow to completely Dry.

Use filtered tips for all pipetting.

All glass vials must be flat-bottomed and screw-cap between 1.5-5 ml volume.

Para-film all glass screw cap reaction vials when reaction requires stirring-overnight.

Surface functionalization of silica beads was prepared as prescribed by Brendan Toohey.

The ultrasonication during the wash steps and the dissolving of PVP is not essential Surface Functionalization Silica Beads 1. Thoroughly clean a round bottom flask ×1 with acetone and ×2 with 2-propanol.
2. Add 20 ml of 2-propanol to the cleaned round bottom flask and set up in a heating mantle, use plastic lid clips to keep any lids fastened and begin to push water through the shlenk line.
3. The 2-propanol is required to be heated to 80° C. under constant stirring for reaction to take place optimally, thus with a thermometer constantly monitor the temperature of the 2-propanol until it reaches temperature, make sure thermometer is wiped with ethanol before each temperature check.
4. Once temperature is reached add 20 μl of APS and 0.1 g of untreated Bang's Beads which equates to 1 ml of the manufacturer's bead slurry and cook for 2 hours under constant stirring.
5. Following cooking transfer contents of flask to appropriate flasks for washing.
6. Wash ×2 in 2-propanol then resuspend in 10 ml Milli-Q water and seal vial with parafilm.

| PART A: Preparing the PVP | | | |
|---|---|---|---|
| Step | Essential | Recommended | Avoid |
| 1. Weigh out required amount of PVP (60 PVP molecules per nm$^2$ of S.A. of silica spheres used) in 15 ml screw cap glass vial | | | |
| 2. Dissolve in 2 ml of the 9:1 (9 ml) CHCl$_3$: (1 ml) 2-propanol solvent under gentle stirring for 1 hour or shake and vortex until media appears clear | Media with dissolved PVP appears clear PVP is thoroughly dissolved | Following suspension of PVP in 1-2 ml of solvent, shake & vortex Prepare PVP an hour before use by dissolving under stirring | Heating during ultrasonication Excessive ultrasonication over 15 min |
| 3. Recombine with stock 9:1 solution | | | |

| PART B: Passivating Nanocrystals to functionalized 5 μm Silica Beads | | | |
|---|---|---|---|
| Step | Essential | Recommended | Avoid |
| 1. Mix 200-500 μl APS/MPS functionalized SiO$_2$ slurry ((0.02 g/ml) & 50-200 μl Qdots in 1.5 ml Eppendorf tube | Shake manually for 1-2 minutes | APS functionalized silica beads have higher affinity for the quantum dots | Not Shaking |
| 2. Put On Motorized wheel at Min-rpm | At least 15 min-1 Hour Min-rpm | Allow to rotate for 1 hour | |
| 3. Add 2-propanol to break the 2 phases shake, vortex then centrifuge @ 3600 rpm 10 secs then discard the supernatant | Shake, Vortex & centrifuge @ 3600 rpm for 10 secs Check that pellet fluoresces under UV light | | |
| 4. Resuspend pellet in CHCl$_3$, shake and Ultrasonicate (Blitz) then centrifuge @ 3600 rpm 10 secs. Discard the supernatant and repeat wash | Shake vigorously and ultrasonicate Check that pellet fluoresces under UV light when supernatant has been discarded after final wash, if it does continue onto step 5, otherwise start again | Can also use 2-propanol as the wash solvent | |
| 5. Resuspend washed pellet in PVP solution prepared in PART A, then combine with stock PVP solution & Ultrasonicate briefly then allow to stir over night. | Resuspend the washed pellet with a portion (1-2 ml) of PVP solution and pipette 2-3 times to maximize sample recovery then combine with stock PVP solution Use a 15 ml screw cap glass-vial for reaction vessel | Add resuspended pellet under-stirring | |

-continued

| PART B: Passivating Nanocrystals to functionalized 5 μm Silica Beads | | | |
|---|---|---|---|
| Step | Essential | Recommended | Avoid |
| 6. Allow to stir overnight. If sample is successful wash x2 in 2-propanol then cover with aluminium foil and store at 4° C. | Seal screw-cap vial with Para-film Smooth stir motion No heating | | Concave Bottom vials |

| PART C: TEOS Coating of PVP capped Nanocrystal-dopped microspheres | | | |
|---|---|---|---|
| Step | Essential | Recommended | Avoid |
| 1. Take 1-5 ml of your PVP capped microsphere sample | | Ultrasonicate (only Blitz) sample | |
| 2. Combine 1:1 with stock 4.2% $NH_3$ solution (e.g. 1 ml of PVP capped bead then 1 ml of 4.2% $NH_3$ solution) | | | |
| 3. Under stirring administer 100 μl of TEOS [5 μl pure TEOS in 1 ml 2-propanol (1:200 solution)] solution to the $NH_3$/PVP Microsphere solution and allow to stir overnight. | Add TEOS while tip is within media but add to side of vial or centre of reaction media Seal screw-cap vial with Para-film Flat-Bottom screw-cap vial Smooth stirring-motion NO HEATING! | | Concave Bottom vials |
| 4. Following successful TEOS coating wash process can be performed with 2-propanol i.e. add 1 ml 2-propanol, shake well, ultrasonicate (Blitz), then centrifuge sample @ 3600 rpm for 10 s and discard supernatant and resuspend in fresh 2-propanol. | Cover sample with aluminum foil and store @ 4° C. Repeat wash at least 3x | | |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any to or more of said steps or features.

BIBLIOGRAPHY

Baird and Myszka, *J Mol Recognit* 14:261-268, 2001;
Casu, *Ann NY Acad Sci* 556:1-17, 1989;
Casu, *Adv Carbohydr Chem Biochem* 43:51-134, 1985;
Conrad, *Heparin binding proteins* Academic Press, San Diego, 1998;
Faham et al. *Science* 271:1116-1120, 1996;
Karlsson and Stahlberg, *Anal Biochem* 228.274-280, 1995;
Lander and Selleck, *J Cell Biol* 148(2):227-232, 2000;
Li et al. *Science* 299:840-843, 2003;
Lin et al. *Science* 278:840-843, 1997;
Lyon et al. *J Biol Chem* 269:11216-11223, 1994;
Maccarana et al. *J Biol Chem* 268(32):23898-23905, 1993;
Malmqvist, *Nature* 361:186-187, 1993;
Rich and Myszka, *J Mol Recognit* 15:352-376, 2002;
Sasisekharan and Venkataraman, *Curr Opin Chem Biol* 4(6): 626-631, 2000;
Vollmer et al. *Biophysical Journal* 85:1974-1979, 2003;
Whisstock et al. *J Mol Biol* 301:1287-1305, 2000;

What is claimed is:

1. A method of detecting multiple analytes in a sample, said method comprising:
   (a) contacting multiple sets of microspheroidal particles with a sample putatively comprising said analytes, wherein each particle within a set of microspheroidal particles comprises an optically detectable label conjugated to an outer surface of the microspheroidal particles and an immobilized putative binding partner or binding partners of an analyte, wherein each set of microspheroidal particles has a different immobilized binding partner or binding partners of an analyte, a different microspheroidal particle size, and a different optically detectable label, and wherein each particle set has a defined Whispering Gallery Mode (WGM) profile, wherein binding of an analyte to said immobilized binding partner or binding partners results in a change in said WGM profile indicated by a spectral shift in the optically detectable label of a set of microspheroidal particles, which is indicative of the presence of said analyte, and (b) detecting binding of analytes to said multiple sets of microspheroidal particles by using a confocal microscope or an array scanner in conjunction with a spectrometer to detect spectral shifts in the WGM profiles of each set of microspheroidal particles, wherein said spectral shifts are in one or more emission peaks of each optically detectable label.

2. The method of claim 1, wherein one or more optically detectable label is a flurochrome.

3. The method of claim 2, wherein each set of microspheroidal particles is labeled with a different flurochrome.

4. The method of claim 1 wherein said microspheroidal particles comprise a material selected from the group consisting of silica, latex, titania, tin dioxide, yttria, alumina, other binary metal oxides, perovskites, other piezoelectric metal oxides, sucrose, agarose and other polymers.

5. The method of claim 4, wherein said microspheroidal particles comprise silica.

6. The method of claim 1 wherein said microspheroidal particles are substantially spherical or spheroidal.

7. The method of claim 1 wherein said microspheroidal particles comprise a diameter of about 300 nm to about 30 µm.

8. The method of claim 1 wherein one or more optically detectable label is a molecule, atom or ion which emits fluorescence.

9. The method of claim 1 wherein one or more optically detectable label is a molecule, atom or ion which emits phosphorescence.

10. The method of claim 1 wherein one or more optically detectable label is a molecule, atom or ion which emits incandescence.

11. The method of claim 1 wherein one or more optically detectable label is detectable in any one or more of the ultraviolet, visible, near infrared (NIR) and/or infrared (IR) wavelength ranges.

12. The method of claim 8 wherein one or more optically detectable label is detectable in the visible wavelength range.

13. The method of claim 1 wherein one or more optically detectable label comprises a label selected from the group consisting of a fluorophore, a semiconductor particle, a phosphor particle, a doped particle, a nanocrystal and a quantum dot.

14. The method of claim 13 wherein the one or more optically detectable label is a fluorophore.

15. The method of claim 13 wherein the one or more optically detectable label is a quantum dot.

16. The method of claim 1, wherein said immobilized binding partner or binding partners comprise a nucleic acid molecule.

17. The method of claim 16 wherein said nucleic acid molecule comprises DNA.

18. The method of claim 16 wherein said nucleic acid molecule comprises RNA.

19. The method of claim 1, wherein said immobilized binding partner or binding partners comprise a peptide, polypeptide or protein.

20. The method of claim 19, wherein said peptide, polypeptide or protein is an enzyme.

21. The method of claim 19, wherein said peptide, polypeptide or protein is an antibody.

22. The method of claim 1, wherein said immobilized binding partner or binding partners comprise a carbohydrate molecule.

23. The method of claim 22, wherein said carbohydrate molecules are glycosaminoglycan molecules.

24. The method of claim 1 wherein the change in said WGM profile comprises a red-shift of one or more peaks in said profile.

25. The method of claim 1 wherein the change in said WGM profile comprises a blue-shift of one or more peaks in the profile.

26. The method of claim 24 wherein the red-shift comprises a wavelength change of said peak or peaks of between 1 and 100 nm.

27. The method of claim 26 wherein the red-shift comprises a wavelength change of said peak or peaks of between 1 and 20 nm.

28. The method of claim 1 wherein the change in said WGM profile comprises the appearance of one or more peaks in one or more of said WGM profile.

29. The method of claim 1 wherein the change in said WGM profile comprises the disappearance of one or more peaks in one or more of said WGM profile.

30. The method of claim 1 wherein the WGM profile is determined by a device which measures light from the microspheroidal particles in conjunction with a spectrometer.

31. The method of claim 30, wherein the device in a flow cytometer.

32. The method of claim 25 wherein the blue-shift comprises a wavelength change of said peak or peaks of between 1 and 100 nm.

33. The method of claim 32 wherein the blue-shift comprises a wavelength change of said peak or peaks of between 1 and 20 nm.

34. The method of claim 5, wherein said particles comprise quantum dots.

* * * * *